United States Patent
Segawa et al.

(10) Patent No.: US 8,343,039 B2
(45) Date of Patent: Jan. 1, 2013

(54) CAPSULE MEDICAL DEVICE

(75) Inventors: Hidetake Segawa, Hachioji (JP); Ayako Nagase, Uenohara (JP); Hironao Kawano, Machida (JP); Seiichiro Kimoto, Akiruno (JP)

(73) Assignee: Olympus Medical Systems Corp., Tokyo (JP)

( * ) Notice: Subject to any disclaimer, the term of this patent is extended or adjusted under 35 U.S.C. 154(b) by 436 days.

(21) Appl. No.: 12/533,466

(22) Filed: Jul. 31, 2009

(65) Prior Publication Data

US 2010/0030025 A1   Feb. 4, 2010

(30) Foreign Application Priority Data

Jul. 31, 2008  (JP) ................................ 2008-198856

(51) Int. Cl.
  *A61B 1/00*  (2006.01)
  *A61B 1/04*  (2006.01)
  *A61B 1/06*  (2006.01)
(52) U.S. Cl. ................ 600/130; 600/109; 600/160
(58) Field of Classification Search ............ 600/109, 600/160; 429/162
  See application file for complete search history.

(56) References Cited

U.S. PATENT DOCUMENTS

| | | | | |
|---|---|---|---|---|
| 4,092,464 A * | 5/1978 | Dey et al. | | 429/127 |
| 6,782,290 B2 * | 8/2004 | Schmidt | | 607/2 |
| 7,662,093 B2 * | 2/2010 | Gilad et al. | | 600/160 |
| 7,985,500 B2 * | 7/2011 | Root et al. | | 429/162 |
| 2007/0118012 A1 * | 5/2007 | Gilad | | 600/109 |
| 2009/0306633 A1 * | 12/2009 | Trovato et al. | | 604/891.1 |

FOREIGN PATENT DOCUMENTS

| | | |
|---|---|---|
| JP | 05-021086 | 1/1993 |
| JP | 05-121099 | 5/1993 |
| JP | 2000-215864 | 8/2000 |
| JP | 2006-149689 A | 6/2006 |
| JP | 2007-181516 | 7/2007 |
| JP | 2008-109847 A | 5/2008 |

OTHER PUBLICATIONS

Japanese Office Action dated Oct. 9, 2012 from related Japanese Patent Application No. 2008-198856, together with an English language translation.

* cited by examiner

*Primary Examiner* — Philip R Smith
*Assistant Examiner* — William Chou
(74) *Attorney, Agent, or Firm* — Scully Scott Murphy & Presser, PC

(57) ABSTRACT

A capsule medical device includes a capsule casing that contains an illumination board, an imaging board, a transmission board, and a control board on which functional components are mounted, and a sheet-like battery that supplies power to the functional components. The sheet-like battery is rolled up to be a pole shape and located between cutout parts of the imaging board, the transmission board, and the control board and the inner wall of the capsule casing.

3 Claims, 14 Drawing Sheets (SHEET SHAPE) (POLE SHAPE)

(SHEET SHAPE) (POLE SHAPE)

CAPSULE MEDICAL DEVICE

CROSS-REFERENCE TO RELATED APPLICATIONS

This application is based upon and claims the benefit of priority from Japanese Patent Application No. 2008-198856, filed Jul. 31, 2008, the entire contents of which are incorporated herein by reference.

BACKGROUND OF THE INVENTION

1. Field of the Invention

The present invention relates to a capsule medical device, and, in particular, to a located position and the shape of a battery included in the capsule medical device.

2. Description of the Related Art

In conventional endoscopy technology, capsule medical devices that have imaging and wireless transmission functions inside capsule casings have been well known. In general, such a capsule medical device is introduced inside the body of a subject and obtains information inside the subject.

The capsule medical device is wireless unlike the usual endoscopes and contains power source, e.g., a battery. An example of such capsule medical device is disclosed in Japanese Patent Application Laid-open (JP-A) No. 2007-181516. The capsule medical device disclosed in JP-A No. 2007-181516 includes a flexible sheet-like battery, e.g., a lithium polymer battery, and the battery is rounded along the inner surface of its cylindrical capsule casing.

The capsule medical device disclosed in JP-A No. 2007-181516, which uses the sheet-like battery as the power source, is reduced in size and weight. The capsule medical device requires a circuit unit into which various boards are integrated, so that the sheet-like battery can be located inside the capsule medical device.

SUMMARY OF THE INVENTION

A capsule medical device according to an aspect of the present invention includes a capsule casing that contains more than one circuit board on which functional components are mounted; and a rolled-up sheet-like battery that supplies power to the functional components, the battery being disposed between a periphery of the circuit board and an inner wall of the capsule casing.

A capsule medical device according to another aspect of the present invention includes a capsule casing that contains more than one circuit board on which functional components are mounted; and a sheet-like battery that comprises an electrode terminal to supply power to the functional components, the electrode terminal being embedded in the capsule casing so as to be exposed to an inner side of the capsule casing.

A capsule medical device according to still another aspect of the present invention includes a capsule casing that contains more than one circuit board on which functional components are mounted; and a sheet-like battery that comprises an electrode terminal, is folded and disposed between circuit boards facing each other, pushes the electrode terminal against at least one of the circuit boards facing each other with elasticity for returning to a state previous to the folding, and supplies power to the functional components via the electrode terminal being pushed.

A capsule medical device according to still another aspect of the present invention includes a capsule casing that contains two or more circuit boards on which functional components are mounted; and a sheet-like battery that maintains a distance between the circuit boards and supplies power to the functional components.

A method of manufacturing a capsule medical device, according to still another aspect of the present invention includes rolling up at least a sheet-like battery in a pole shape; and disposing the battery between a circuit board of the battery and an inner wall of a capsule casing of the capsule medical device.

A method of manufacturing a capsule medical device according to still another aspect of the present invention includes embedding at least a sheet-like battery in a capsule casing; and containing the circuit board in the capsule casing in which the battery is embedded.

A method of manufacturing a capsule medical device according to still another aspect of the present invention includes folding at least a sheet-like battery; and disposing the folded battery between the circuit boards facing each other.

A method of manufacturing the capsule medical device according to still another aspect of the present invention includes forming at least a sheet-like battery in a cylindrical shape; and disposing the cylindrically-formed battery between the circuit boards facing each other.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of a capsule medical device in which a sheet-like battery of the present invention is located in a predetermined manner are described with reference to the accompanying drawings. The description below, however, does not limit the scope of the present invention.

First Embodiment

Figure 1:
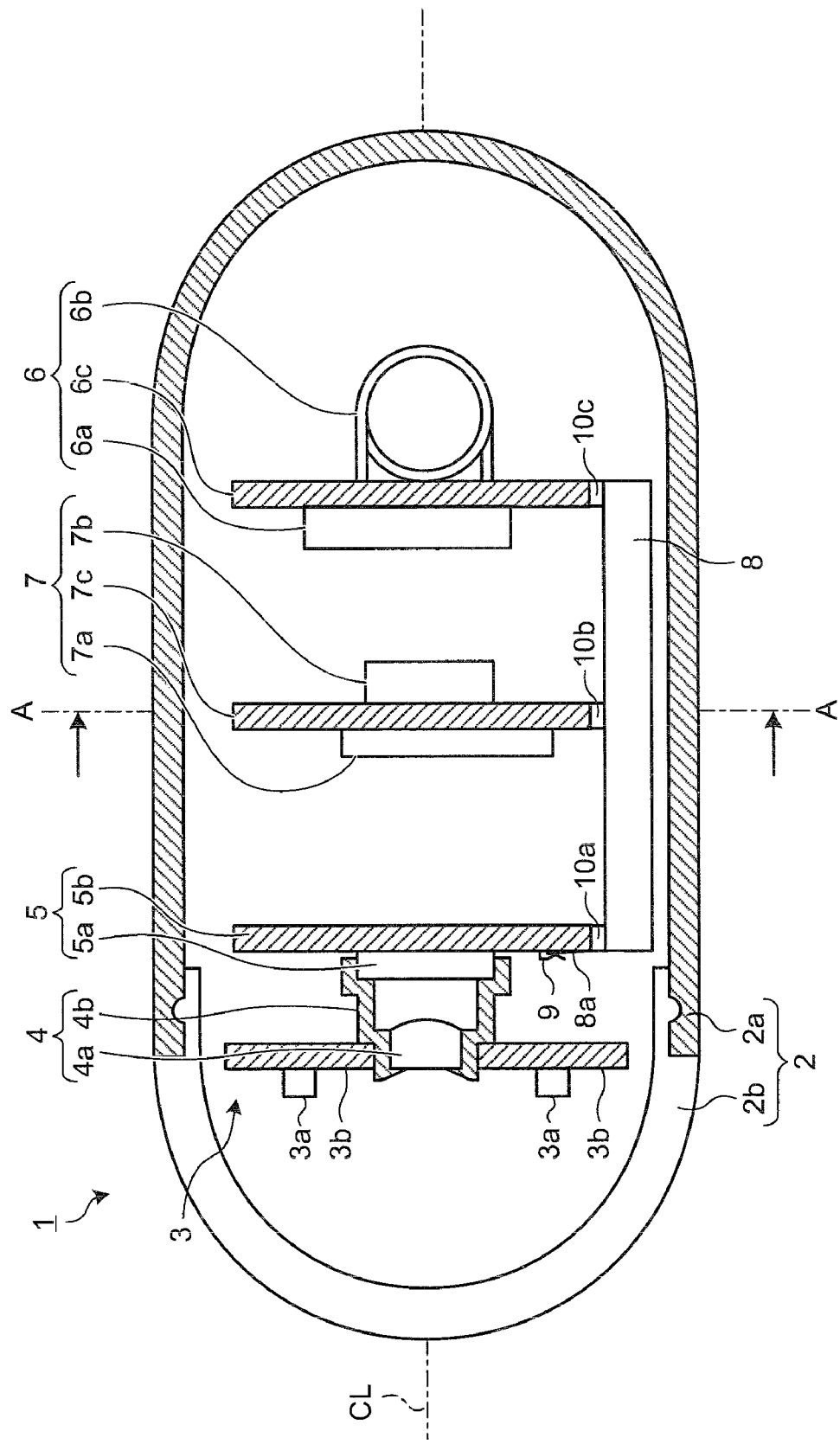
FIG. 1 is a schematic diagram of an exemplary configuration of a capsule medical device in accordance with a first embodiment of the present invention.
Figure 2:
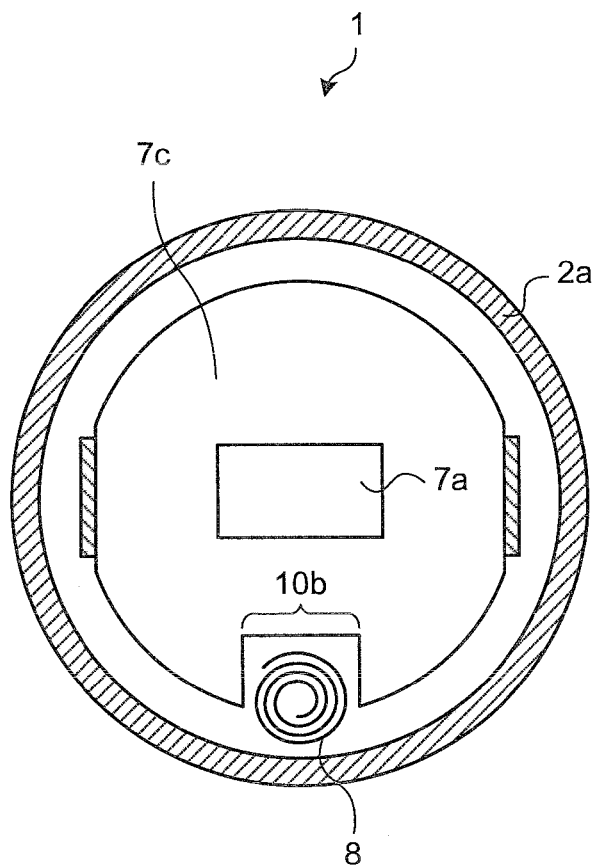
FIG. 2 is a schematic cross-sectional diagram of the capsule medical device shown in FIG. 1 taken along the line A-A.

FIG. 1 is a schematic diagram of an exemplary configuration of a capsule medical device in accordance with a first embodiment of the present invention. FIG. 2 is a schematic cross-sectional diagram of the capsule medical device shown in FIG. 1 taken along the line A-A. A capsule medical device 1 shown in FIGS. 1 and 2 includes a capsule casing 2, an illuminating unit 3, an optical system 4, an imaging unit 5, a wireless-transmission unit 6, a control unit 7, and a sheet-like battery 8. The illuminating unit 3 illuminates a photographic subject. The optical system 4 forms an optical image of the photographic subject that is illuminated by the illuminating unit 3. The imaging unit 5 captures an image of the photographic subject, i.e., an in-vivo image of the subject. The wireless-transmission unit 6 wirelessly transmits the in-vivo image that has been captured by the imaging unit 5 to the outside. The control unit 7 controls operations of each of the components included in the capsule medical device 1. The sheet-like battery 8 supplies power to each of the components in the capsule medical device 1. The components of the capsule medical device of the present invention are not limited to the above. For example, the capsule medical device may not include a light-emitting unit depending on the function of the imaging unit. Each of the components is described in detail below.

The capsule casing 2 has at least a function for protecting the inner components of the capsule medical device. The shape of the capsule casing 2 is not limited to a certain shape. For example, the capsule casing 2 can be a cylinder shape whose ends are dome-shaped as shown in FIG. 1. When the inner components of the capsule medical device are vulnerable to water, it is preferable that the capsule casing 2 be airtight. The materials for the capsule casing 2 are not limited to certain materials. For example, the capsule casing 2 may be made of resins. When the imaging unit 5 that obtains information inside the body has a function for obtaining optical information, it is preferable that a part of the capsule casing 2 be optically transparent. For example, a dome-shaped casing 2b, which is a hemispherical part and dome-shaped, may be made of transparent materials as shown in FIG. 1.

The illuminating unit 3 emits illumination light, which is visible light such as white light, toward the inside of organs of the subject so that the inside of organs, i.e., the photographic subject of the imaging unit 5, is illuminated. In detail, the illuminating unit 3 includes more than one light-emitting unit 3a that emits the illumination light, and an illumination board 3b that includes a circuit for the functions of the illuminating unit 3.

The light-emitting units 3a are light-emitting devices such as LEDs, which emit illumination light toward the subject of the imaging unit 5. The light-emitting units 3a emit illumination light through the dome-shaped casing 2b toward the photographic subject of the imaging unit 5. The illumination board 3b is a rigid circuit board that has a disk shape and includes circuits for the function of the light-emitting units 3a. There is an opening substantially in a middle part of the illumination board 3b, and the optical system 4 is to be inserted into the opening. The light-emitting units 3a are located on the mount surface of the illumination board 3b, i.e., the board surface facing the dome-shaped casing 2b so that the light-emitting units 3a surround the opening.

The optical system 4 condenses reflection light received from the inside of the organ of the subject illuminated by the illumination light of the light-emitting units 3a, i.e., condenses the reflection light from the photographic subject of the imaging unit 5, into the light-receiving surface of the imaging unit 5. In detail, the optical system 4 includes a lens 4a that condenses light into the light-receiving surface of the imaging unit 5, and a lens frame 4b that retains the lens 4a.

The lens frame 4b includes a cylinder structure whose ends are open. The lens frame 4b retains the lens 4a that is arranged in its cylinder structure. The upper part of the lens frame 4b is fixed as the upper part is inserted through the opening of the illumination board 3b while the lower part of the lens frame 4b is fixed to a solid imaging device 5a of the imaging unit 5. The lens 4a is fixed near the opening in the upper part of the lens frame 4b. The lens 4a condenses reflection light received from the photographic subject of the imaging unit 5 into the light-receiving surface of the imaging unit 5 so that an optical image of the photographic subject is formed on the light-receiving surface. It is preferable that the optical axis of the optical system 4 be consistent with the central axis CL along the longitudinal direction of the capsule casing 2, which is along the longer part of the capsule casing 2.

The imaging unit 5 captures images of the inside of organs of the subject, i.e., images of the photographic subject illuminated by the illumination light from the light-emitting units 3a described above. Thus, the imaging unit 5 captures an in-vivo image of the subject. In detail, the imaging unit 5 includes the solid imaging device 5a such as a CCD and CMOS image sensor, and an imaging board 5b for the functions of the imaging unit 5.

The imaging board 5b is a rigid circuit board that has a substantially disk shape and includes a cutout part 10a that is located at a part in the periphery facing the sheet-like battery 8. The components such as the solid imaging device 5a that are necessary for the imaging function to capture the in-vivo image are mounted on the imaging board 5b. The solid imaging device 5a is mounted on the mount surface of the imaging board 5b and fixed to the opening in the lower part of the lens frame 4b as described above. The solid imaging device 5a receives reflection light that is condensed by the optical system 4 and transmitted via the light-receiving surface from the photographic subject. The solid imaging device 5a performs a photoelectric conversion on the reflection light received from the photographic subject so that the image of the photographic subject, i.e., the in-vivo image of the subject is captured.

The wireless-transmission unit 6 wirelessly transmits the in-vivo images of the subject that are captured by the imaging unit 5 sequentially to the receiving apparatus (not shown) that is located outside the subject. In detail, the wireless-transmission unit 6 includes a transmission processing unit 6a that performs a transmission process such as a modulation process on the image signal of the in-vivo image, an antenna 6b that wirelessly transmits the in-vivo image of the subject to the outside, and a transmission board 6c that includes circuits for the functions of the wireless-transmission unit 6.

The transmission board 6c is a rigid circuit board that has a substantially disk shape and includes the cutout part 10a that is located at a part in the periphery facing the sheet-like battery 8. In this case, the antenna 6b is mounted on one of the mount surfaces of the transmission board 6c, i.e., the mount surface facing the dome-shaped part of a cylindrical casing 2a. The transmission processing unit 6a obtains from the control unit 7 the image signal that includes data of the in-vivo image of the subject captured by the imaging unit 5. The transmission processing unit 6a performs transmission processes such as a modulation process on the obtained image signal to generate a wireless signal including the image signal. The transmission processing unit 6a transmits the generated wireless signal to the outside via the antenna 6b. The in-vivo image of the subject that is wirelessly transmitted via the antenna 6b is received by the receiving apparatus that is located outside the subject.

The control unit 7 controls each of the components of the capsule medical device 1. In detail, the control unit 7 includes an operation control unit 7a, a power control unit 7b, and a control board 7c. The operation control unit 7a controls the operations of the illuminating unit 3, the imaging unit 5, and the wireless-transmission unit 6. The power control unit 7b controls the power supply to the illuminating unit 3, the imaging unit 5, and the wireless transmission unit 6. The control board 7c includes circuits for the functions of the control unit 7.

The control board 7c is a rigid circuit board that has a substantially disk shape and includes a cutout part 10b that is located in the periphery facing the sheet-like battery 8. The components such as the operation control unit 7a and the power control unit 7b that are necessary for the control functions are mounted on the control board 7c.

The operation control unit 7a includes a CPU that executes predetermined processing programs, a ROM that previously stores various types of data such as a white balance, and a RAM that stores calculation parameters and the like. The operation control unit 7a controls the operations of the components of the capsule medical device 1, i.e., the illuminating unit 3, the imaging unit 5, and the wireless-transmission unit 6. Furthermore, the operation control unit 7a controls input and output of signals among those components. In detail, the operation control unit 7a controls the operation timings of the light-emitting units 3a and the solid imaging device 5a so that the image of the inside of the organs that is illuminated by the illumination light, i.e., the in-vivo image, is captured. Furthermore, the operation control unit 7a obtains the signal on which the photoelectric conversion has been performed by the solid imaging device 5a and performs a predetermined signal process on the obtained signal to generate the image signal including the data of the in-vivo image of the subject. Every time the image signal is generated, i.e., every time the in-vivo image is captured by the imaging unit 5, the operation control unit 7a controls the transmission processing unit 6a of the wireless-transmission unit 6 so that the transmission processing unit 6a transmits the wireless signal including the image signal to the outside.

The power control unit 7b is a switch circuit for switching power source to ON or OFF, a regulator, and the like. The power control unit 7b switches the ON state to the OFF state or vice versa according to a magnetic field applied from the outside. When the power control unit 7b is in the ON state, power is supplied from the sheet-like battery 8 to the illuminating unit 3, the imaging unit 5, the wireless-transmission unit 6, and the operation control unit 7a as needed. When the power control unit 7b is on the OFF state, the power supply to the components of the capsule medical device 1 is stopped. The switching of the ON or OFF state by the power control unit 7b may not necessarily be performed according to the magnetic field from the outside, and, for example, may be performed according to the optical signal such as infrared light received from the outside.

Figure 3:
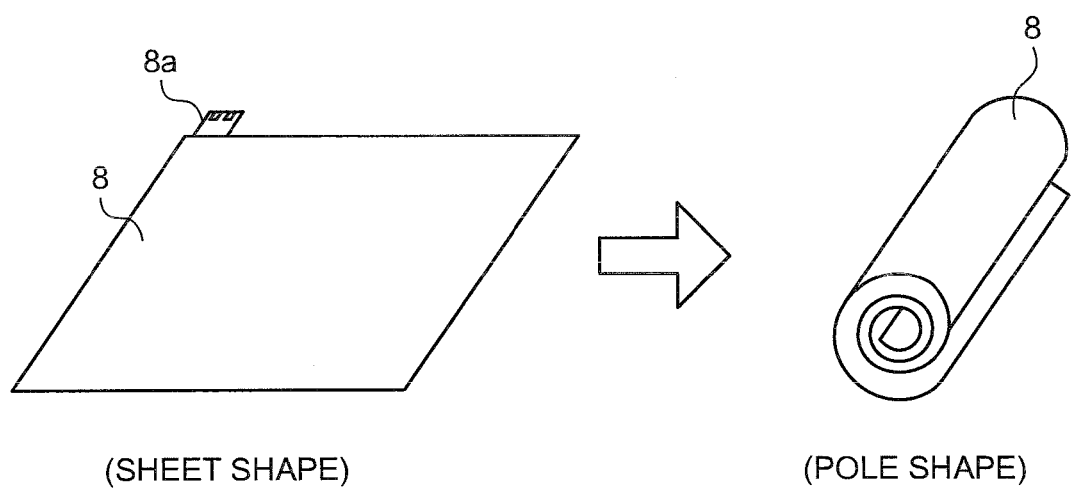
FIG. 3 is a schematic diagram in which a sheet-like battery in accordance with the first embodiment of the present invention is rolled up, changing its sheet shape into a pole shape.

The sheet-like battery 8 is a flexible sheet-like battery such as a lithium polymer battery. The sheet-like battery 8 functions as power source that supplied power to the illuminating unit 3, the imaging unit 5, the wireless-transmission unit 6, and the control unit 7 described above. FIG. 3 is a schematic diagram in which the sheet-like battery is rolled up, changing its sheet shape into a pole shape. The sheet-like battery 8 is very thin and light compared with a silver oxide battery, e.g., a button-shaped battery, and a dry-cell battery. The sheet-like battery 8 is rolled up, changes its sheet shape into a pole shape as shown in FIG. 3, and then is located inside the capsule casing 2. As shown in FIGS. 1 and 2, the sheet-like battery 8, which is rolled up and a pole shape, is located between the periphery of the imaging board 5b, the control board 7c, and the transmission board 6c, and the inner wall of the capsule casing 2. In this case, it is preferable that the sheet-like battery 8, which is rolled up and a pole shape, be located in a manner such that the longitudinal axis of the sheet-like battery is in parallel with the central axis CL along the longitudinal axis of the capsule casing 2. The sheet-like battery 8 includes an electrode terminal 8a that enables an electrical connection. When the electrode terminal 8a is connected with a clip terminal 9 on the imaging board 5b, the sheet-like battery 8 is electrically connected with the illumination board 3b, the imaging board 5b, the transmission board 6c, and the control board 7c.

Although not shown in FIG. 1, the illumination board 3b, the imaging board 5b, the transmission board 6c, and the control board 7c described above are electrically connected with each other on the flexible circuit board and the like. The illumination board 3b, the imaging board 5b, the transmission board 6c, and the control board 7c that are connected on the flexible circuit board and the like constructs as a whole a circuit board on which functional components are mounted. The cutout parts 10a to 10c are formed in the periphery of the imaging board 5b, the transmission board 6c, and the control board 7c so that the circuit wirings are not blocked. In detail, the cutout part 10b in the control board 7c is an example of a cutout part where electrical components and circuit wirings are not arranged and which is located in the periphery of the control board 7c facing the sheet-like battery 8. For example, as shown in FIG. 2, the cutout part 10b is an cutout area larger than the diameter of the sheet-like battery 8 being rolled up to be a pole shape. The cutout part 10a in the imaging board 5b and the cutout part 10c in the transmission board 6c are similar to the cutout part 10b in the control board 7c shown in FIG. 2.

The sheet-like battery 8, which is rolled up to be a pole shape, is located in space surrounded by the cutout parts 10a to 10*c* in the imaging board 5*b*, the transmission board 6*c*, and the control board 7*c*, and by the inner wall of the capsule casing 2. The space surrounded by the peripheries of the imaging board 5*b*, the transmission board 6*c*, and the control board 7*c* and by the inner wall of the capsule casing 2 is used for the arrangement of the sheet-like battery 8, which is rolled up to be a pole shape.

Power from the sheet-like battery 8 is supplied to the functional components of the illumination board 3*b*, the imaging board 5*b*, the transmission board 6*c*, and the control board 7*c* as needed via the electrode terminal 8*a* and the clip terminal 9 described above. Power from the sheet-like battery 8 is supplied to the light-emitting units 3*a*, the solid imaging device 5*a*, the transmission processing unit 6*a*, the operation control unit 7*a*, and the power control unit 7*b* as needed.

Figure 4:
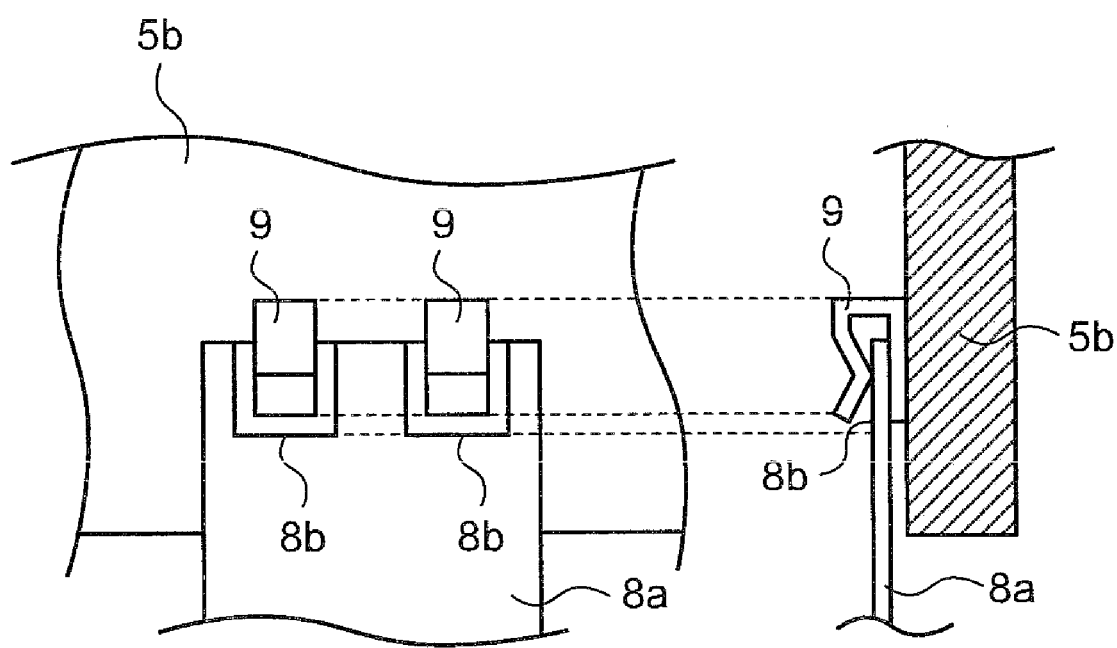
FIG. 4 is a schematic diagram in which a clip terminal of a circuit board is connected with an electrode terminal of the sheet-like battery in accordance with the first embodiment of the present invention.

The connection between the electrode terminal 8*a* of the sheet-like battery 8 and the clip terminal 9 is described. FIG. 4 is a schematic diagram in which the electrode terminal of the sheet-like battery is connected with the clip terminal of the circuit board. As shown in FIG. 4, the clip terminal 9 is a clip-shaped power terminal that is made of elastic conductive materials and is located on the imaging board 5*b* and near the cutout part 10*a*. The clip terminal 9 clips edges of the electrode terminal 8*a* and retains two electrodes 8*b* on the edge of the electrode terminal 8*a* using elasticity of the clip terminal 9. The two electrodes 8*b* that are clipped by the clip terminal 9 are electrically connected with the imaging board 5*b* via the clip terminal 9.

Because the electrodes 8*b* of the sheet-like battery 8 are clipped by the clip terminal 9, it is not necessary to solder the electrodes 8*b* of the sheet-like battery 8 to the power terminals of the circuit boards such as the imaging board 5*b*. As a result, the sheet-like battery 8 can be electrically connected with the circuit boards (the illumination board 3*b*, the imaging board 5*b*, the transmission board 6*c*, and the control board 7*c*) of the capsule medical device 1 easily. Thus, the connection between the sheet-like battery 8 and each of the functional components of the illumination board 3*b*, the imaging board 5*b*, the transmission board 6*c*, and the control board 7*c* can be established easily. In detail, the sheet-like battery can be easily connected with the light-emitting units 3*a*, the solid imaging device 5*a*, the transmission processing unit 6*a*, the operation control unit 7*a*, the power control unit 7*b*, and the like.

As described above, in the first embodiment of the present invention, the cut parts such as the cutout parts are formed in the peripheries of the circuit boards on which the functional components are mounted. In the first embodiment, the sheet-like battery that supplies power to the functional components is rolled up to be a pole shape and is arranged between the cut part that is formed in the periphery of the circuit board and the inner wall of the capsule casing that contains the circuit board. Thus, in the first embodiment, the inner space in the capsule casing that is located between the periphery of the circuit board of the capsule casing and the inner wall of the capsule casing can be used effectively as the sheet-like battery is arranged therein. Therefore, the capsule medical device can be made smaller in size without reducing power required for operations of the functional components arranged in the capsule casing and without reducing the operation time of the functional components.

Furthermore, in the first embodiment of the present invention, the clip terminal is arranged on the circuit boards such as the imaging board 5*b* described above. The clip terminal of the circuit boards clips the electrode of the sheet-like battery so that the sheet-like battery is electrically connected with the circuit boards of the capsule medical device. Thus, in the first embodiment, it is not necessary to perform soldering or the like to connect the electrode of the sheet-like battery to the power terminal of the circuit boards by soldering. As a result, in the first embodiment, the electrode of the sheet-like battery, the connection between the sheet-like battery and the circuit board can be easily established as the clip terminal clips the electrode of the sheet-like battery. Thus, the sheet-like battery can be electrically connected with the functional components of the circuit boards in the capsule medical device easily. As a result, production cost of the capsule medical device can be reduced, and the capsule medical device containing the sheet-like battery can be easily assembled.

Furthermore, because the sheet-like battery that is arranged in the capsule casing as power source is thin and light compared with the button-shaped battery that includes a metal case as its outer package, the power source of the capsule medical device can be reduced in weight. Therefore, in the first embodiment, the capsule medical device can be reduced in weight.

As described, according to the first embodiment, the capsule medical device that includes the sheet-like battery can be easily produced.

Second Embodiment

A second embodiment of the present invention is described. In the first embodiment described above, the cutout parts 10*a* to 10*c* are formed in the peripheries of the imaging board 5*b*, the control board 7*c*, and the transmission board 6*c* so that the sheet-like battery 8 being rolled up to be a pole shape can be arranged. In contrast, in the second embodiment, the sheet-like battery 8 includes openings corresponding to the periphery of the circuit boards. The peripheries of the circuit boards are inserted into the openings of the sheet-like battery 8 that is contained in the capsule casing 2, respectively.

Figure 5:
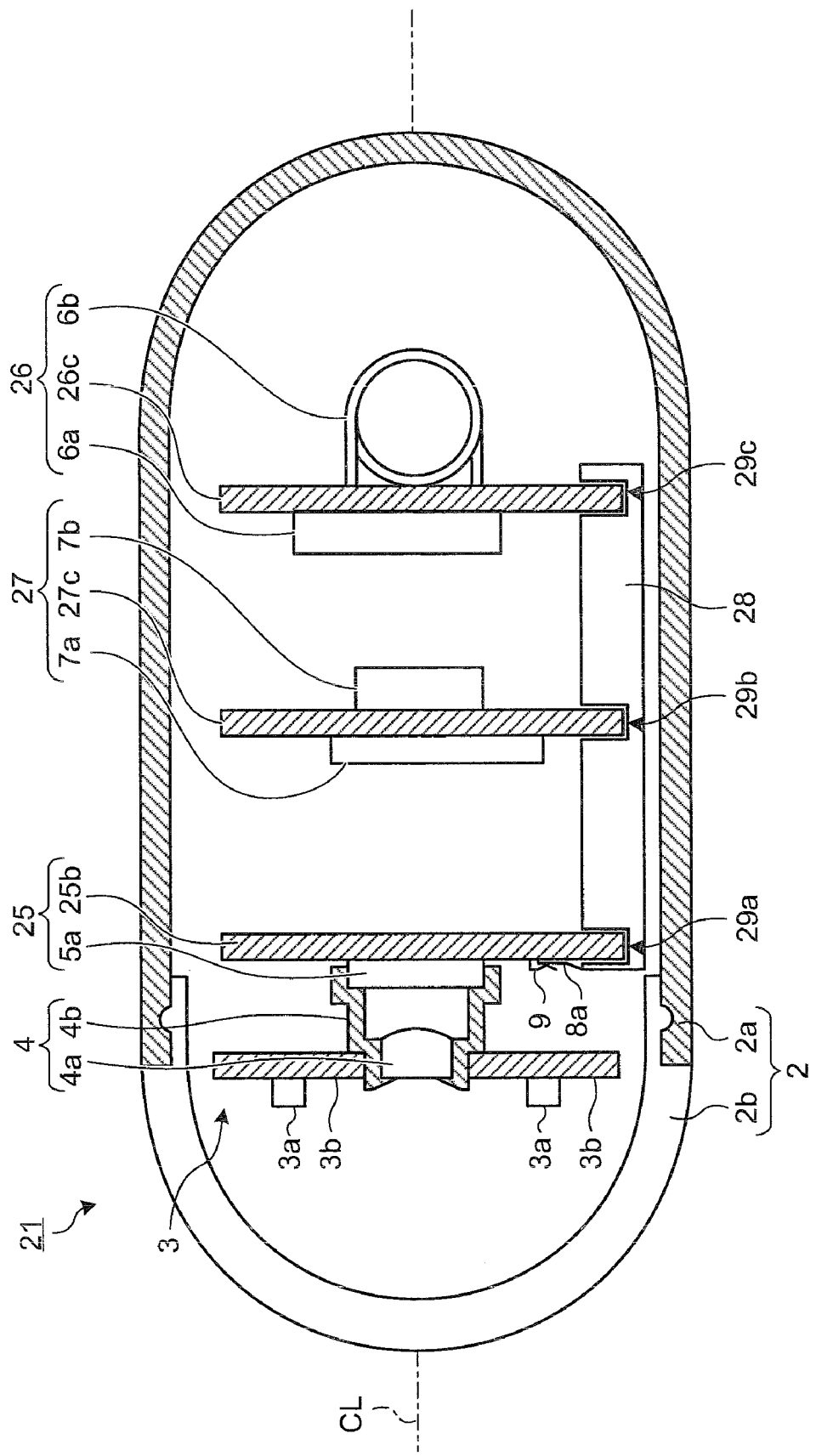
FIG. 5 is a schematic diagram of an exemplary configuration of a capsule medical device in accordance with a second embodiment of the present invention.

FIG. 5 is a schematic diagram of an exemplary configuration of a capsule medical device in accordance with the second embodiment of the present invention. As shown in FIG. 5, a capsule medical device 21 in accordance with the second embodiment includes an imaging unit 25 instead of the imaging unit 5 included in the capsule medical device 1 in accordance with the first embodiment. Furthermore, the capsule medical device 21 includes a control unit 27 instead of the control unit 7 included in the capsule medical device 1. Furthermore, the capsule medical device 21 includes a sheet-like battery 28 instead of the sheet-like battery 8 included in the capsule medical device 1. In the capsule medical device 21, the imaging unit 25 includes, instead of the imaging board 5*b* in the first embodiment, an imaging board 25*b* that has a disk shape and does not include the cutout part 10*a*. A wireless-transmission unit 26 includes, instead of the transmission board 6*c* in the first embodiment, a transmission board 26*c* that has a disk shape and does not include the cutout part 10*c*. The control unit 27 includes, instead of the control board 7*c* in the first embodiment, a control board 27*c* that has a disk shape and does not include the cutout part 10*b*. Other configurations are the same as those of the first embodiment, and same components have same numerals.

The imaging board 25*b* is a rigid circuit board that has a disk shape. The imaging board 25*b* does not include the cutout part 10*a* in the periphery, and other configurations are the same as the imaging board 5*b* in the first embodiment. In this case, the clip terminal 9 is located in the periphery of the imaging board 25*b* and near the part facing the sheet-like battery 28.

The transmission board 26c is a rigid circuit board that has a disk shape. The transmission board 26c does not include the cutout part 10c in the periphery, and other configurations are the same as the transmission board 6c in the first embodiment. The control board 27c is a rigid circuit board that has a disk shape. The control board 27c does not include the cutout part 10b in the periphery, and other configurations are the same as the control board 7c in the first embodiment.

Although not shown in FIG. 5, the illumination board 3b, the imaging board 25b, the transmission board 26c, and the control board 27c are connected with each other via a flexible circuit board or the like similarly to the first embodiment described above. In detail, the illumination board 3b, the imaging board 25b, the transmission board 26c, and the control board 27c construct as a whole a circuit board on which functional components of the capsule medical device 21 are mounted.

The sheet-like battery 28 includes openings 29a to 29c into which the circuit boards, i.e., the imaging board 25b, the transmission board 26c, and the control board 27c, of the capsule medical device 21 described above. Other configurations are the same as the sheet-like battery 8 in the first embodiment described above.

Figure 6:
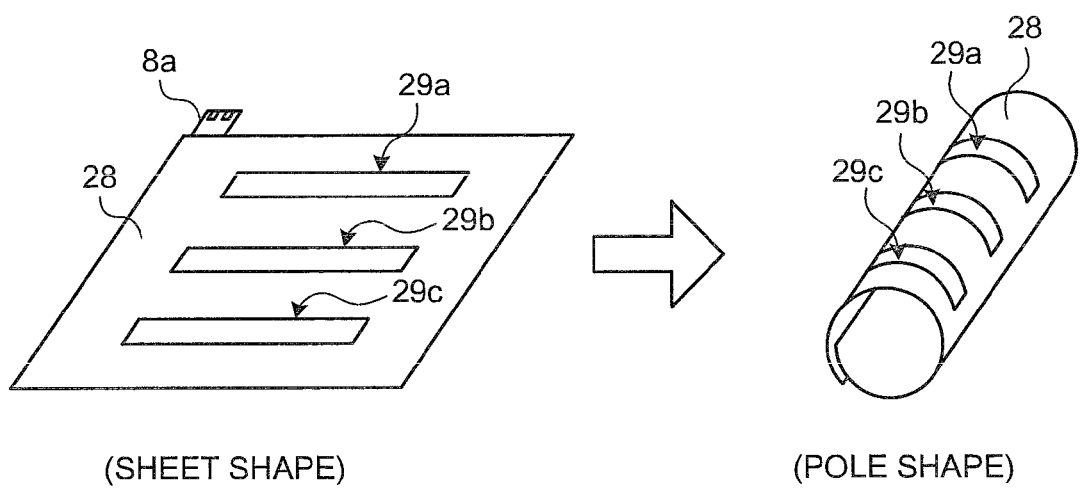
FIG. 6 is a schematic diagram in which a sheet-like battery having openings in accordance with the second embodiment of the present invention is rolled up, changing its sheet shape into a pole shape.

FIG. 6 is a schematic diagram in which the sheet-like battery that includes openings is rolled up, changing its sheet shape into a pole shape. As shown in FIG. 6, the openings 29a to 29c are formed in the sheet-like battery 28 corresponding to the imaging board 25b, the transmission board 26c, and the control board 27c, respectively. The openings 29a to 29c are, for example, rectangular. Those three openings 29a to 29c in the sheet-like battery 8 are formed in the respective areas facing the imaging board 25b, the transmission board 26c, and the control board 27c. The sheet-like battery 28 is previously rolled up and changes its sheet shape into a pole shape as shown in FIG. 6 before the sheet-like battery 28 is located inside the capsule casing 2. In this case, the sheet-like battery 28 is rolled up in a manner such that the openings 29a to 29c are arranged corresponding to the arrangement of the imaging board 25b, the transmission board 26c, and the control board 27c.

The sheet-like battery 28, which is rolled up to be a pole shape, is located between the peripheries of the imaging board 25b, the control board 27c, and the transmission board 26c, and the inner wall of the capsule casing 2 as shown in FIG. 5. In this case, the edge of the imaging board 25b is inserted into the opening 29a, the edge of the control board 27c is inserted into the opening 29c, and the edge of the transmission board 26c is inserted into the opening 29c. The edges of the circuit boards are inserted into the openings 29a to 29c of the sheet-like battery 8, respectively, and the sheet-like battery 8 is electrically connected with the illumination board 3b, the imaging board 25b, the transmission board 26c, and the control board 27c as the electrode terminal 8a is connected with the clip terminal 9 similarly to the first embodiment. Furthermore, the sheet-like battery 28 determines the relative positions of the boards as to where the illumination board 3b, the imaging board 25b, the transmission board 26c, and the control board 27c are located. It is preferable that the longitudinal axis of the sheet-like battery 28 be in parallel with the central axis CL along the longitudinal axis of the capsule casing 2.

As described above, in the second embodiment of the present invention, the openings in the sheet-like battery are formed in the areas corresponding to the arrangement of the circuit boards on which the functional components are mounted. Furthermore, in the second embodiment, the sheet-like battery is arranged inside the capsule casing in a manner such that the edges of the circuit boards are inserted into the openings in the sheet-like battery, respectively. Other configurations are the same as those of the first embodiment. Thus, without the cut part being formed in the periphery of the circuit board, the sheet-like battery, which is rolled up to be a pole shape, can be easily arranged inside the casing, between the peripheries of the circuit boards in the capsule casing and the inner wall of the capsule casing. Furthermore, in the second embodiment, the relative positions among the circuit boards can be easily determined. The capsule medical device can have the same operation benefits as the first embodiment described above, can adjust distance among the circuit boards in the capsule casing, and therefore can be assembled more easily.

Third Embodiment

A third embodiment of the present invention is described. In the first and second embodiments described above, the sheet-like battery that is rolled up is arranged located between the inner wall of the capsule casing and the peripheries of the circuit boards. In contrast, in the third embodiment, the sheet-like battery is embedded in the capsule casing with the electrode terminal being exposed.

Figure 7:
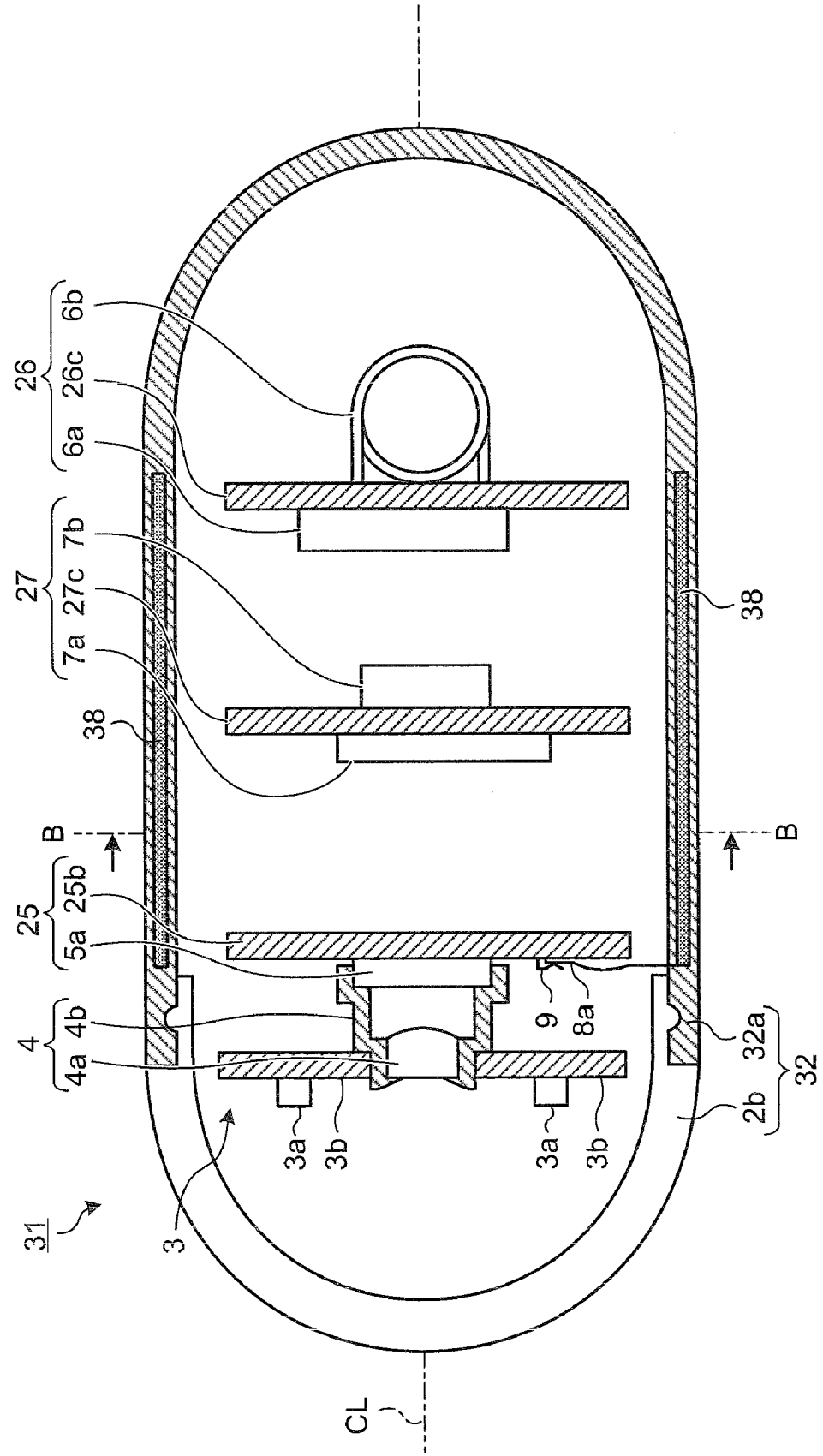
FIG. 7 is a schematic diagram of an exemplary configuration of a capsule medical device in accordance with a third embodiment of the present invention.
Figure 8:
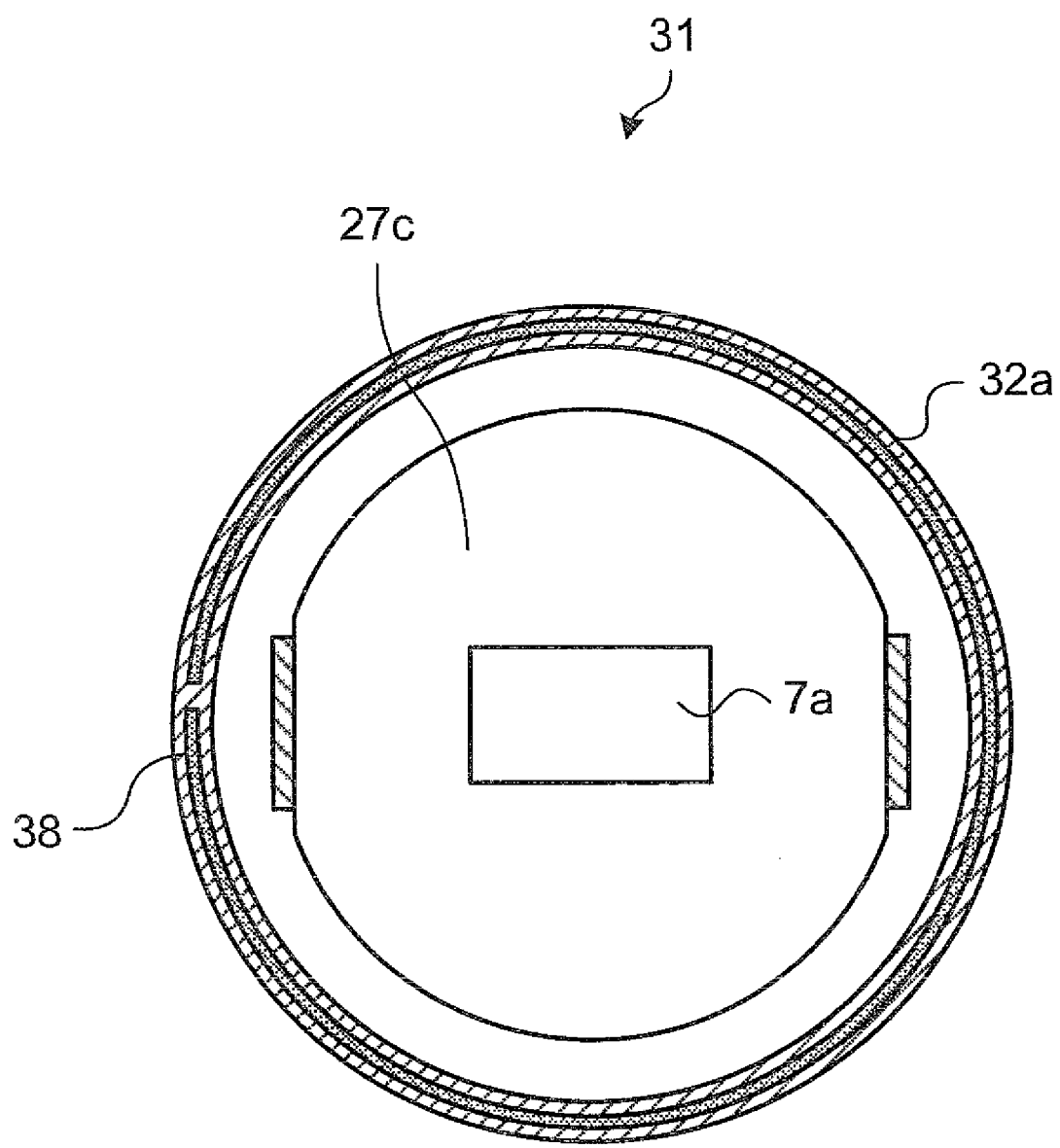
FIG. 8 is a schematic cross-sectional diagram of the capsule medical device shown in FIG. 7 taken along the line B-B.

FIG. 7 is a schematic diagram of an exemplary configuration of a capsule medical device in accordance with the third embodiment of the present invention. FIG. 8 is a schematic cross-sectional diagram of the capsule medical device shown in FIG. 7 taken along the line B-B. As shown in FIGS. 7 and 8, a capsule medical device 31 in accordance with the third embodiment includes a capsule casing 32 and a sheet-like battery 38 instead of the capsule casing 2 and the sheet-like battery 28 in accordance with the second embodiment described above. The capsule casing 32 includes, instead of the cylindrical casing 2a in the second embodiment, a cylindrical casing 32a in which the sheet-like battery 38 is embedded. The open end of the cylindrical casing 32a is sealed by the dome-shaped casing 2b. Other than the embedding of the sheet-like battery 38, the cylindrical casing 32a has the same configuration as the cylindrical casing 2a in the second embodiment described above. The sheet-like battery 38 is embedded, through the insert process and the molding process, in the cylindrical casing 32a in a manner such that the electrode terminal 8a is exposed on a side of the inner wall of the casing so that the cylindrical casing 32a is united with the sheet-like battery 38. Other than the embedding of the sheet-like battery 38, the cylindrical casing 32a has the same configuration as the cylindrical casing 2a in the second embodiment described above.

Other than the embedding in the capsule casing, the sheet-like battery 38 is the same as the sheet-like battery 8 in the first embodiment described above. In detail, the sheet-like battery 38 includes the electrode terminal 8a similarly to the sheet-like battery 8 shown in FIG. 3. The sheet-like battery 38 is embedded in the cylindrical casing 32a in a manner such that the electrode terminal 8a is exposed on a side of the inner wall of the capsule casing 32. The sheet-like battery 38, which is embedded in the cylindrical casing 32a, has a cylinder shape depending on the shape of the cylindrical casing 32a as shown in FIGS. 7 and 8. The electrode terminal 8a of the sheet-like battery 38 is exposed to a side of the inner wall of the cylindrical casing 32a and is connected with the clip terminal 9, whereby the sheet-like battery 38 is electrically connected with the circuit boards of the capsule medical device 31. In detail, those circuit boards of the capsule medical device 31 are the illumination board 3b, the imaging board 25b, the transmission board 26c, and the control board 27c.

As described, in the third embodiment of the present invention, the sheet-like battery is embedded in the cylindrical casing in a manner such that the electrode terminal of the sheet-like battery for the connection with the circuit boards on which the functional components are mounted is exposed to a side of the inner wall of the capsule casing. Further, in the third embodiment, the open end of the cylindrical casing in which the sheet-like battery is embedded is sealed by the dome-shaped casing. Other configurations are the same as those of the second embodiment. In this manner, the sheet-like battery can be embedded, and it is not necessary to form space for the arrangement of the sheet-like battery inside the capsule casing. Furthermore, the number of components is decreased as the capsule casing and the sheet-like battery are united. Thus, similarly to the second embodiment described above, lower weight of power source, improved easy assembling, and lower production cost can be achieved, and the inner space of the capsule casing can be used effectively for the arrangement of the circuit boards on which the functional components are mounted. As described, in the third embodiment, the capsule medical device can be reduced in size.

Fourth Embodiment

A fourth embodiment of the present invention is described. In the first and second embodiments, the sheet-like battery that is rolled up to be a pole shape is located between the inner wall of the capsule casing and the peripheries of the circuit boards. In contrast, in the fourth embodiment, the sheet-like battery is folded and then retained between the circuit boards.

Figure 9:
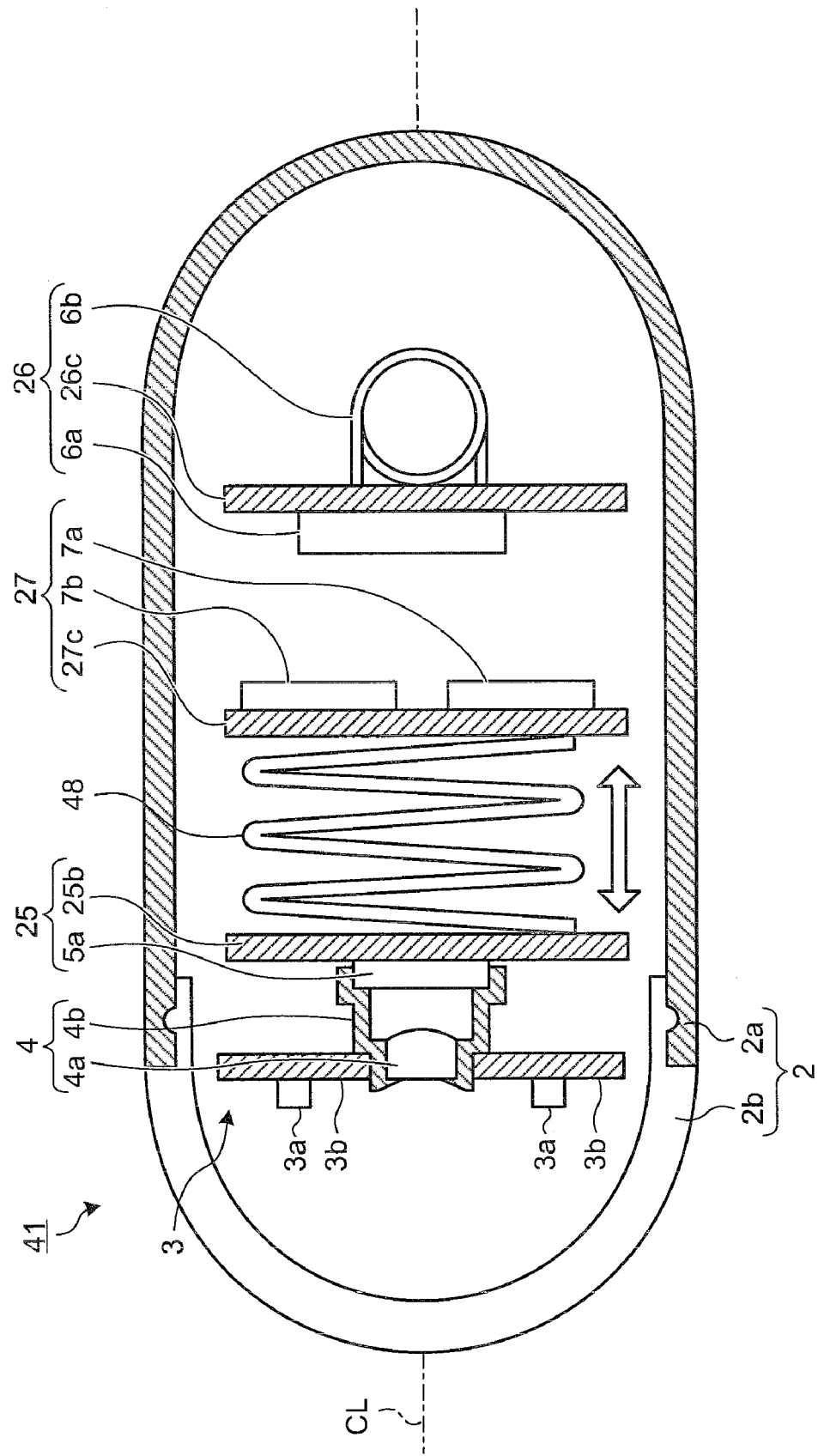
FIG. 9 is a schematic diagram of an exemplary configuration of a capsule medical device in accordance with the fourth embodiment of the present invention.

FIG. 9 is a schematic diagram of an exemplary configuration of the capsule medical device in accordance with the fourth embodiment of the present invention. As shown in FIG. 9, a capsule medical device 41 in accordance with the fourth embodiment includes, instead of the sheet-like battery 28 of the capsule medical device 21 in accordance with the second embodiment described above, a sheet-like battery 48 that is folded. In the capsule medical device 41 in accordance with the fourth embodiment, a power terminal of the circuit boards that is connected with the electrode of the sheet-like battery is located on the board surface of the imaging board 25b, the board surface facing the control board 27c. Furthermore, the functional components on the imaging board 25b and those on the control board 27c are mounted in a manner such that the functional components allow the arrangement of the sheet-like battery 48. Other configurations are the same as those of the second embodiment, and same components have same numerals.

Figure 10:
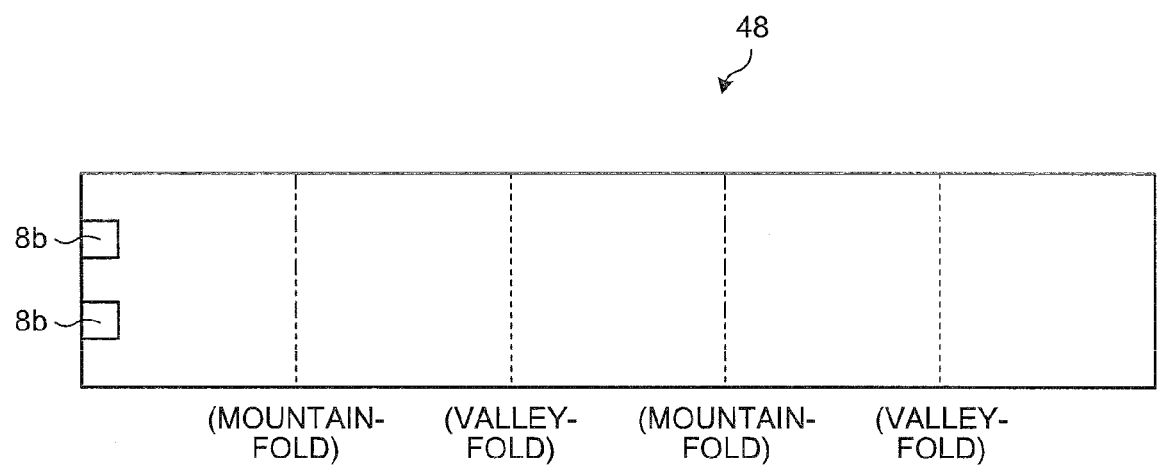
FIG. 10 is a schematic diagram in which a sheet-like battery of the capsule medical device in accordance with the fourth embodiment of the present invention is unfolded.

The sheet-like battery 48 is folded and located between the circuit boards unlike the sheet-like battery 28 in the second embodiment described above. FIG. 10 is a schematic diagram in which the sheet-like battery of the capsule medical device in accordance with the fourth embodiment of the present invention is unfolded. As shown in FIG. 10, the sheet-like battery 48 is rectangular and has the two electrodes 8b at one end. The sheet-like battery 48 is folded with the two electrodes 8b exposed outward. The sheet-like battery 48 that is unfolded as shown in FIG. 10 is folded as it is mountain-folded along the two-dot chain line and valley-folded along the dashed line. The two electrodes 8b are located at one end of the sheet-like battery 48. Not limited to this, the electrodes may be located at the both ends of the sheet-like battery 48, respectively.

The sheet-like battery 48 being folded is retained between the circuit boards of the capsule medical device 41 opposing to each other, for example, between the imaging board 25b and the control board 27c as shown in FIG. 9. The sheet-like battery 48 that is retained between the imaging board 25b and the control board 27c applies elastic force (shown in the thick arrow in FIG. 9) onto the imaging board 25b and the control board 27c as the sheet-like battery 48 tends to change its folded state back into an unfolded state. Due to its elasticity, the sheet-like battery 48 pushes the two electrodes 8b onto the power terminal (not shown) of the imaging board 25b so that the sheet-like battery 48 is electrically connected with the imaging board 25b and that the sheet-like battery 48 is fixed in a position relative to the imaging board 25b and the control board 27c. Thus, the sheet-like battery 48 with the two electrodes 8b attached to the power terminal of the imaging board 25b is electrically connected with the circuit boards of the capsule medical device 41, in detail, with the illumination board 3b, the imaging board 25b, the transmission board 26c, and the control board 27c.

The attachment of the two electrode terminals 8a of the sheet-like battery 48 to the power terminal of the imaging board 25b may be performed using only the elastic force that is applied to the imaging board 25b and the control board 27c as described above. Alternatively, the two electrode terminals 8a may be clipped by the clip terminal 9 that is located no the board surface of the imaging board 25b. As a result, the two electrode terminals 8a of the sheet-like battery 48 can be definitely connected electrically with the power terminal of the circuit boards of the capsule medical device. It is preferable that the clip terminal 9 of the imaging board 25b be located on the board surface of the imaging board 25b, the board surface facing the control board 27c.

As described, in the fourth embodiment, the sheet-like battery that is folded with the electrodes exposed outward is located between the two circuit boards, of the circuit boards on which the functional components are mounted, that face each other. In the fourth embodiment, the sheet-like battery pushes the electrodes onto one of the circuit boards at the ends of the sheet-like battery, using the elasticity of the sheet-like battery as the sheet-like battery tends to change its folded state back into the unfolded state. Furthermore, in the fourth embodiment, the sheet-like battery is electrically connected with the functional components on the circuit boards via the electrodes pushed onto the circuit boards. Other configurations are the same as those of the second embodiment. The sheet-like battery can be definitely connected with the circuit boards using the elasticity of the sheet-like battery that is folded. In this manner, the volume of the sheet-like battery along the longitudinal axis of the capsule casing can be smaller compared with conventional batteries containing a button shaped-battery. As a result, similarly to the second embodiment described above, the power source can be reduced in weight, and the apparatus can be easily assembled and therefore production cost can be lower. The capsule medical device can be reduced in size easily.

Fifth Embodiment

A fifth embodiment of the present invention is described. In the first and second embodiments described above, the sheet-like battery that is rolled up to be a pole shape is located between the inner wall of the capsule casing and the peripheries of the circuit boards. In contrast, in the fifth embodiment, the sheet-like battery that has a cylinder shape is located among the circuit boards so that the sheet-like battery functions as the power source and further as a spacer for maintaining distance among the boards.

Figure 11:
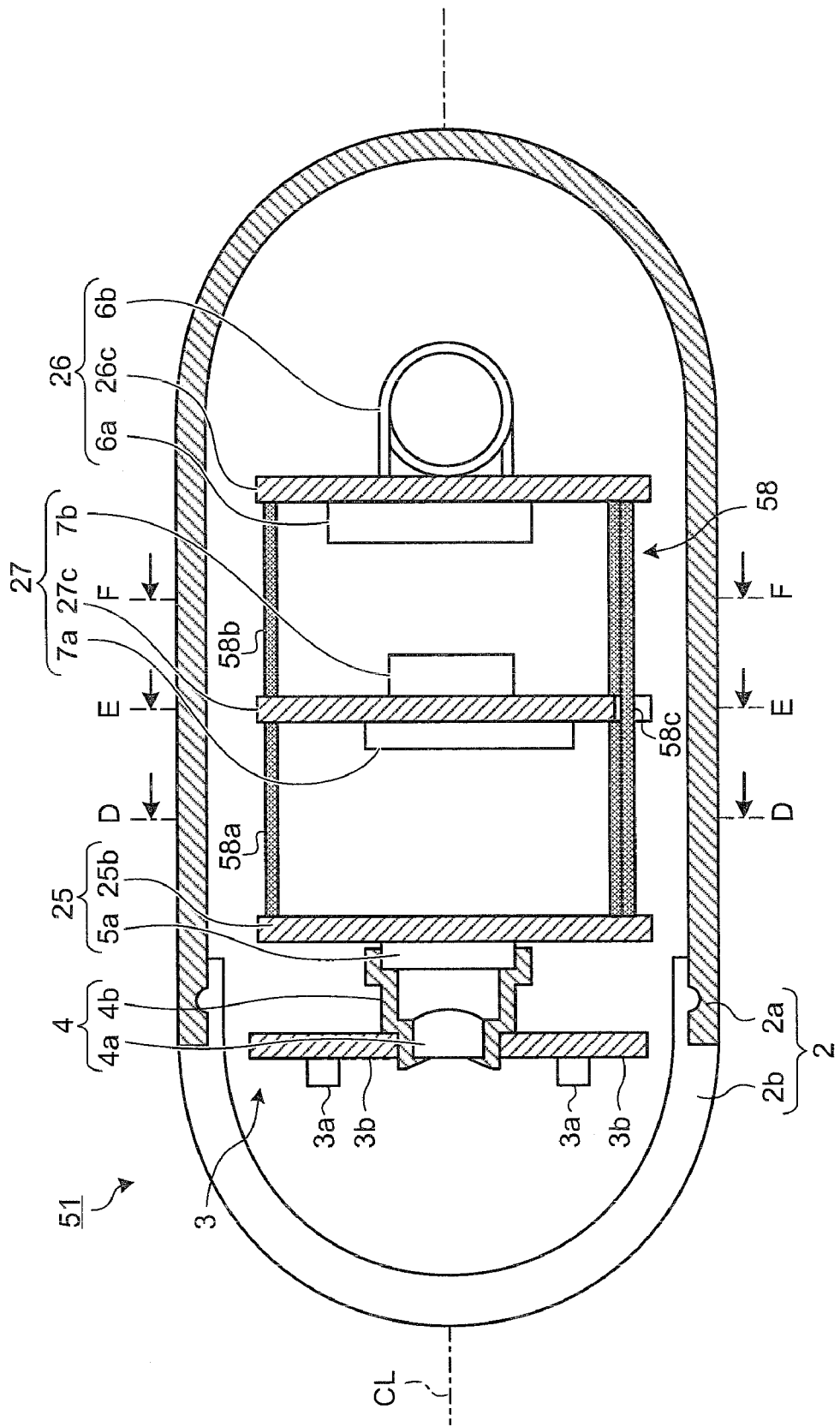
FIG. 11 is a schematic diagram of an exemplary configuration of a capsule medical device in accordance with a fifth embodiment of the present invention.
Figure 12:
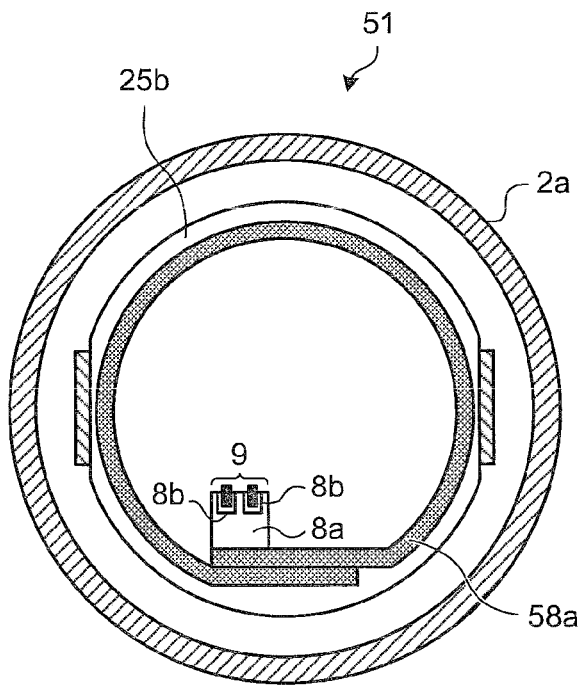
FIG. 12 is a schematic cross-sectional diagram of the capsule medical device shown in FIG. 11 taken along the line D-D.
Figure 13:
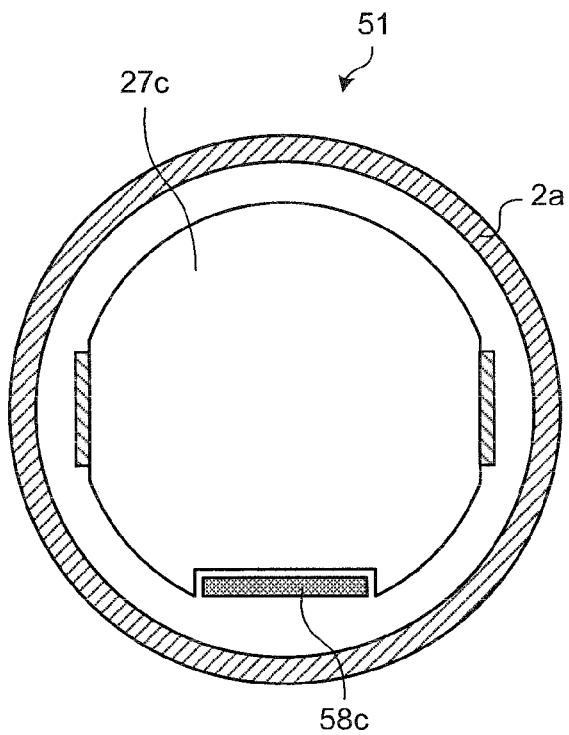
FIG. 13 is a schematic cross-sectional diagram of the capsule medical device shown in FIG. 11 taken along the line E-E.
Figure 14:
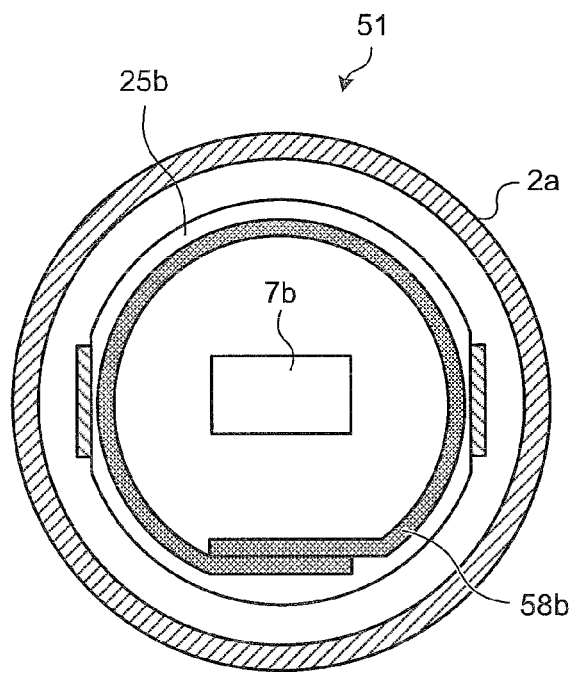
FIG. 14 is a schematic cross-sectional diagram of the capsule medical device shown in FIG. 11 taken along the line F-F.

FIG. 11 is a schematic diagram of an exemplary configuration of a capsule medical device in accordance with the fifth embodiment of the present invention. FIG. 12 is a schematic cross-sectional diagram of the capsule medical device shown in FIG. 11 taken along the line D-D. FIG. 13 is a schematic cross-sectional diagram of the capsule medical device shown in FIG. 11 taken along the line E-E. FIG. 14 is a schematic cross-sectional diagram of the capsule medical device shown in FIG. 11 taken along the line F-F. As shown in FIGS. 11 to 14, a capsule medical device 51 in accordance with the fifth embodiment includes, instead of the sheet-like battery 28 in the second embodiment described above, a sheet-like battery 58 that has a cylinder shape. Other configurations are the same as those of the second embodiment, and same components have same numerals.

The sheet-like battery 58 that has a cylinder shape is located among the circuit boards facing each other unlike the sheet-like battery 28 in the second embodiment described above. The sheet-like battery 58 functions as a spacer for maintaining the distance among the circuit boards and also as the power source.

Figure 15:
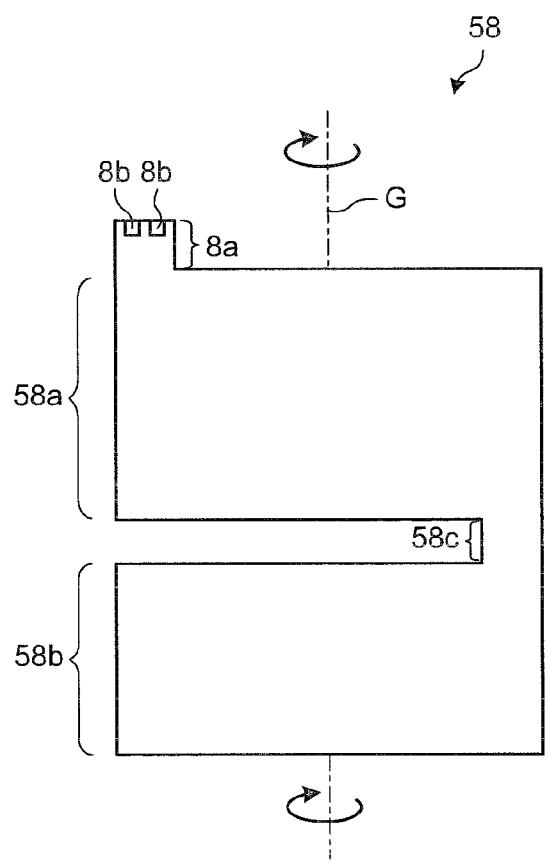
FIG. 15 is a schematic diagram in which the sheet-like battery of the capsule medical device in accordance with the fifth embodiment of the present invention is unfolded.

FIG. 15 is a schematic diagram in which the sheet-like battery of the capsule medical device in accordance with the fifth embodiment of the present invention is unfolded. As shown in FIG. 15, the sheet-like battery 58 includes cylinder components 58a and 58b, a bar-like part 58c that connects the cylinder components 58a and 58b together, and the electrode terminal 8a that is extended from the edge of the cylinder component 58a.

The cylinder components 58a and 58b are a battery function unit and are connected together in series by the bar-like part 58c. For example, both the cylinder components 58a and 58b are rolled around an axis G so that the cylinder components 58a and 58b become cylinder shapes having the substantially same longitudinal axis. The outer diameter of the cylinder component 58a that becomes a cylinder shape is equal to or smaller than the size of the imaging board 25b and the control board 27c. The inner diameter of the cylinder component 58a is equal to or larger than the area where the functional components of the imaging board 25b and the control board 27c are mounted. Furthermore, the length of the cylinder of the cylinder component 58a is equal to or larger than the distance between the imaging board 25b and the control board 27c, the distance required for enough space for the arrangement of the functional components. The cylinder component 58a that has the cylinder shape is located and retained between the imaging board 25b and the control board 27c as shown in FIGS. 11 and 12. Therefore, the cylinder component 58a maintains distance between the imaging board 25b and the control board 27c so that there is definitely enough space for the arrangement of the functional components. In this case, the functional components on the imaging board 25b and those on the control board 27c are located inside the cylinder component 58a that has a cylinder shape.

The outer diameter of the cylinder component 58b is equal to or smaller than size of the control board 27c and the transmission board 26c. The inner diameter of the cylinder component 58b is equal to or larger than the area where the functional components of the control board 27c and the transmission board 26c are mounted. The length of the cylinder of the cylinder component 58b is equal to or larger than the distance between the control board 27c and the transmission board 26c, the distance required for enough space for the arrangement of the functional components. As shown in FIGS. 11 and 14, the cylinder component 58b is located and retained between the control board 27c and the transmission board 26c and maintains the distance between the control board 27c and the transmission board 26c so that there is definitely enough space for the arrangement of the functional components. In this case, the functional parts on the control board 27c and those on the transmission board 26c are located inside the cylinder component 58b that has the cylinder shape.

The bar-like part 58c is a power function unit and is continuous among the cylinder components 58a and 58b described above. As shown in FIG. 15, the bar-like part 58c connects the cylinder components 58a and 58b together. The bar-like part 58c is located in the periphery of the control board 27c and connects the cylinder components 58a and 58b together that become a cylinder shape. In this case, as shown in FIG. 13, the bar-like part 58c is located in the cutout part that is formed in the periphery of the control board 27c.

As shown in FIG. 12, the electrode terminal 8a of the sheet-like battery 58 is clipped by the clip terminal 9 that is located on the board surface of the imaging board 25b. Because the two electrodes 8b of the electrode terminal 8a are clipped by the clip terminal 9 similarly to the first embodiment and other embodiments, the electrodes 8b are electrically connected with the clip terminal 9 easily. The sheet-like battery 58 is connected, via the electrode terminals 8a and the clip terminal 9, with the circuit boards of the capsule medical device 51, in detail, the illumination board 3b, the imaging board 25b, the transmission board 26c, and the control board 27c.

As described, in the fifth embodiment, the sheet-like battery that has a cylinder shape is located among the circuit boards facing each other on which the functional components are mounted so that the sheet-like battery maintains the distance between the circuit boards. Other configurations are the same as those of the second embodiment. Thus, the sheet-like battery, which is the power source, functions as a spacer for maintaining the distance between the circuit boards. In this manner, a mechanical component such as a spacer is not required, and a number of components can be reduced. As a result, the capsule medical device has the same operation effects as those of the second embodiment and can definitely maintain the distance between the circuit boards that is required for the arrangement of the functional components easily, whereby the capsule medical device can be easily produced.

In the first embodiment above, the cutout parts 10a to 10c are formed in portions of the peripheries of the circuit boards facing the sheet-like battery so that the sheet-like battery that has a pole shape can be located therein. Not limited to this, in the present embodiment, a D-cut part may be formed in portions of the peripheries of the circuit boards facing the sheet-like battery 8 so that the sheet-like battery can be located therein.

Figure 16:
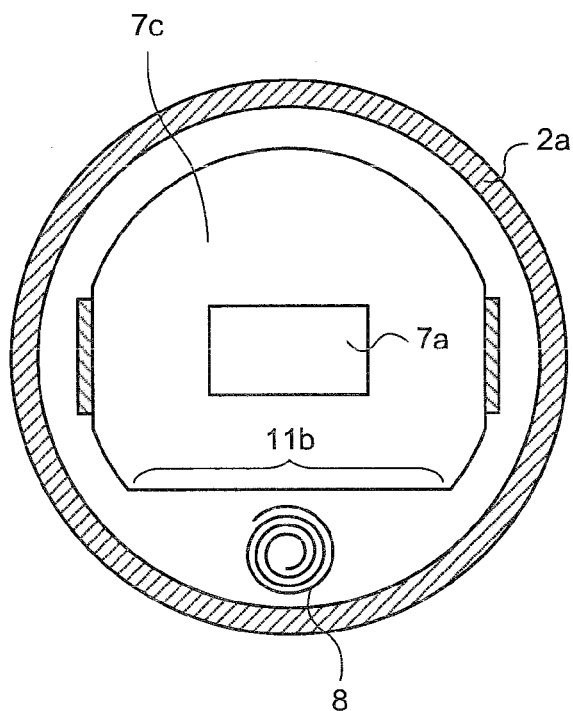
FIG. 16 is a schematic diagram of a D-cut part that is formed on the periphery of a circuit board in accordance with the fifth embodiment of the present invention.

FIG. 16 is a schematic diagram of a D-cut part formed in the periphery of the circuit board. As shown in FIG. 16, a D-cut part 11b of the control board 7c is required as a space for the arrangement of the sheet-like battery 8. The D-cut part 11b is formed by D-cutting the portion of the periphery of the control board 7c, the portion facing the sheet-like battery 8. Although not shown in the figures, D-cut parts similar to the D-cut part 11b of the control board 7c may be formed in the peripheries of the imaging board 5b and the transmission board 6c, respectively. In this case, the sheet-like battery 8 is located between the D-cut parts of the circuit boards and the inner wall of the capsule casing 2.

In the fourth embodiment, the sheet-like battery that has a rectangular shape shown in FIG. 10 is folded and located between the circuit boards. Not limited to this, in the present embodiment, the sheet-like battery that is folded and located between the circuit boards may include a plurality of battery function units that are connected with each other to be a bar shape.

Figure 17:
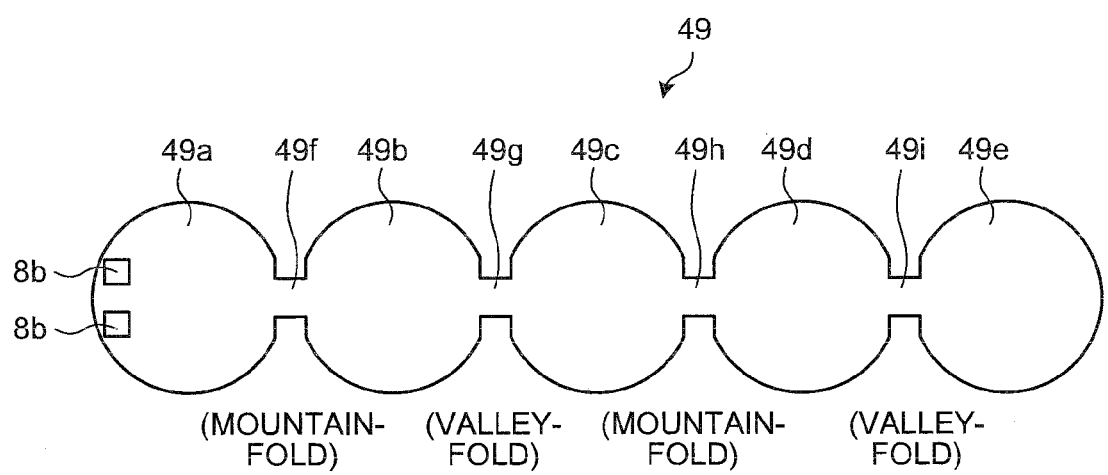
FIG. 17 is a schematic diagram of a variation of the sheet-like battery of the capsule medical device in accordance with the fourth embodiment of the present invention.

FIG. 17 is a schematic diagram of an exemplary configuration of a variation of the sheet-like battery of the capsule medical device in accordance with the fourth embodiment of the present invention. FIG. 17 shows a sheet-like battery that is unfolded. As shown in FIG. 17, a sheet-like battery 49 in accordance with the variation includes a plurality of circle parts 49a to 49e that are circular battery function units corresponding to a shape of the circuit board, and a plurality of bar-like parts 49f to 49i that connect the circle parts 49a to 49e together in series. The two electrodes 8b are located on the circle part 49a of the circle parts 49a to 49e. The sheet-like battery 49 including the circle parts 49a to 49e and the bar-like parts 49f to 49i are folded with the two electrodes exposed outward. The sheet-like battery 49 that is unfolded as shown in FIG. 17 is mountain-folded in the bar-like parts 49f and 49h and valley-folded in the bar-like parts 49g and 49i. The sheet-like battery 49 can have the larger surface area than the rectangular sheet-like battery 48 described above does. Thus, the sheet-like battery 49 can have the larger power capacity than the sheet-like battery 48 does. The capsule medical device 41 in accordance with the fourth embodiment of the present invention may contain, instead of the sheet-like battery 48, the sheet-like battery 49 shown in FIG. 17 that is folded. In this case, the capsule medical device 41 can have the same operation effects as that containing the sheet-like battery 48 and further can improve the power capacity of the power source contained therein with the apparatus being kept small.

In the fifth embodiment described above, the sheet-like battery 58 in which the two cylinder components 58a and 58b are connected together in series by the bar-like part 58c is located between the circuit boards. Not limited to this, in the present embodiment, a plurality of sheet-like batteries may be located in the capsule casing in a manner such that the sheet-like batteries clip the edges of the circuit boards so that the sheet-like batteries function as power sources and also as spacers.

Figure 18:
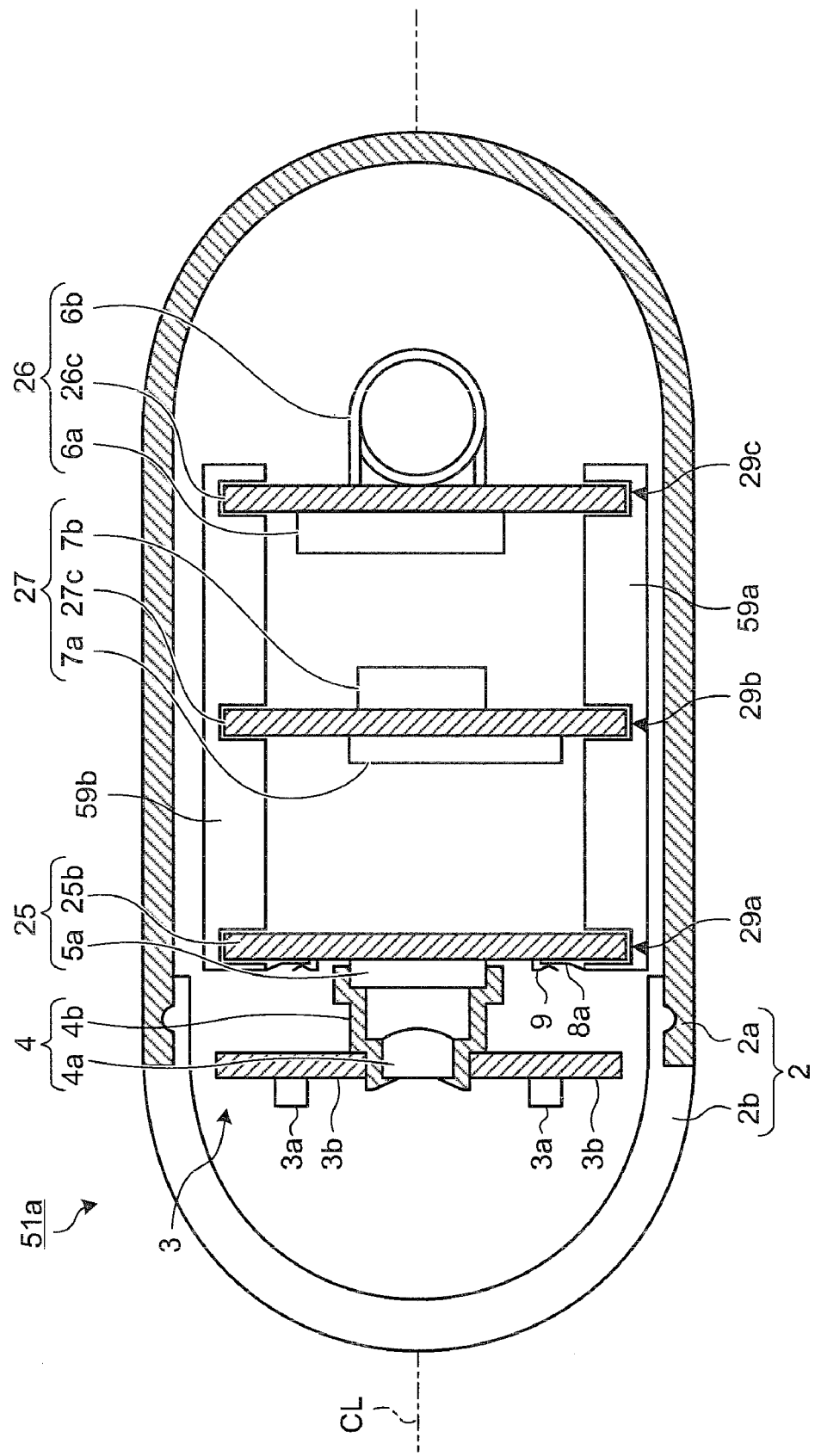
FIG. 18 is a schematic diagram of an exemplary configuration of a variation of the capsule medical device in accordance with the fifth embodiment of the present invention.

FIG. 18 is a schematic diagram of an exemplary configuration of a capsule medical device in accordance with a variation of the fifth embodiment of the present invention. As shown in FIG. 18, a capsule medical device 51a in accordance with the variation of the fifth embodiment includes sheet-like batteries 59a and 59b instead of the sheet-like battery 58 of the capsule medical device 51 in accordance with the fifth embodiment described above. Other configurations are the same as those of the fifth embodiment, and same components have same numerals.

The sheet-like battery 59a has the same structure as the sheet-like battery 28 in the second embodiment described above. The sheet-like battery 59a includes the electrode terminal 8a that is clipped by the clip terminal 9, and the openings 29a to 29c into which the imaging board 25b, the control board 27c, and the transmission board 26c are inserted, respectively. The sheet-like battery 59b is the same as the sheet-like battery 59a. The sheet-like batteries 59a and 59b being a pole shape are located to clip the imaging board 25b, the control board 27c, and the transmission board 26c from both sides. In this case, the edges of the imaging board 25b, the control board 27c, and the transmission board 26c are inserted into the openings of the sheet-like batteries 59a and 59b located on both sides, respectively. The sheet-like batteries 59a and 59b that clip the circuit boards from both sides maintain the distance among the imaging board 25b, the control board 27c, and the transmission board 26c in a substantially similar manner with the fifth embodiment. The capsule medical device 51a that contains the sheet-like batteries 59a and 59b have the same operational effects as the capsule medical device 51 in accordance with the fifth embodiment described above.

In the first to fifth embodiments described above, the electrodes of the sheet-like battery are directly connected with the power terminal of the circuit boards by the clip terminal 9. Not limited to this, the electrodes of the sheet-like battery may be electrically connected with the power terminal of the circuit boards via jumper wires or the like.

In the first to fifth embodiments, the clip terminal that is a power terminal of the circuit boards is located on the imaging board. Not limited to this, in the present embodiment, the clip terminal may be located on any desired one of the circuit boards of the capsule medical device, e.g., the illumination board, the imaging board, the control board, or the transmission board.

In the fourth embodiment described above, the sheet-like battery 48 that is folded is located between the imaging board 25b and the control board 27c. Not limited to this, in the present embodiment, the sheet-like battery 48 may be located between any two circuit boards facing each other. For example, the sheet-like battery being folded may be located between the control board 27c and the transmission board 26c described above.

In the fifth embodiment described above, the sheet-like battery 58 includes the two cylinder components 58a and 58b. Not limited to this, in the present invention, the number of the cylinder components of the sheet-like battery may be only one or more as long as the cylinder component is formed corresponding to the number of circuit boards that needs space for the arrangement of the functional parts.

In the first to fifth embodiments described above, the capsule medical device is monocular type that includes a single imaging unit. Not limited to this, in the present invention, the capsule medical device in accordance with the present invention may be pantoscopic type that includes more than one imaging unit.

In the first to fifth embodiments described above, the capsule medical device captures the in-vivo images of the subject. Not limited to this, the capsule medical device in accordance with the fifth embodiment, may measure a pH value or temperament inside the subject as in-vivo information of the subject. Still another example is that the capsule medical device may detect the state of the living tissues as the in-vivo information of the subject. Still another example is that the capsule medical device in accordance with the present invention may spread or inject medicine into the inside of the subject. Still another example is that the capsule medical device may extract substances inside the body such as living tissue.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method of manufacturing a capsule medical device comprising:
   rolling up at least a sheet-like battery on a pole shape;
   forming an opening in the battery such that the opening extends in a direction perpendicular to a longitudinal axis of the rolled-up sheet-like battery; and
   inserting a periphery of a circuit board into the opening.

2. The method according to claim 1, wherein the longitudinal direction of the rolled-up sheet-like battery is in parallel with a longitudinal direction of a casing of the capsule medical device.

3. The method according to claim 1, wherein the circuit board includes a clip terminal that clips an electrode of the rolled-up sheet-like battery for connection.

* * * * *